United States Patent [19]

Radobolja et al.

[11] 3,939,144
[45] Feb. 17, 1976

[54] MANUFACTURE OF N-(BENZENESULFONYL)-5-O-DESOSAMI-NYL-ERYTHROMYCILAMINE DERIVATIVES

[75] Inventors: Gorjana Radobolja; Zrinka Tamburasev; Slobodan Djokic, all of Zagreb, Yugoslavia

[73] Assignee: Pliva, Pharmaceutical and Chemical Works, Zagreb, Yugoslavia

[22] Filed: Jan. 10, 1975

[21] Appl. No.: 540,151

[30] Foreign Application Priority Data
Jan. 14, 1974 Yugoslavia.............................. 97/74

[52] U.S. Cl.............................. 260/210 E; 424/180

[51] Int. Cl.$^2$........................................ C07H 15/22
[58] Field of Search ................................ 260/210 E

[56] References Cited
FOREIGN PATENTS OR APPLICATIONS
1,100,267   1/1968   United Kingdom ............. 260/210 E Primary Examiner—Johnnie R. Brown
Attorney, Agent, or Firm—Kurt Kelman

[57] ABSTRACT

N-(4-$R^2$-benzenesulfonyl)-5-O-desosaminyl-erythromycilamine, wherein $R^2$ is a $C_1$-$C_5$ alkyl radical, halogen or $NH_2$. The compounds possess antibacterial activity.

5 Claims, No Drawings

MANUFACTURE OF N-(BENZENESULFONYL)-5-O-DESOSAMINYL-ERYTHROMYCILAMINE DERIVATIVES

This invention relates to the manufacture of N-(4-benzenesulfonyl)-5-O-desosaminyl-erythromycilamine derivatives from N-(4-R-benzenesulfonyl)-erythromycilamine by reaction with diluted mineral acids.

According to the invention, there is disclosed a process for the manufacture of novel N-(4-R$^2$-benzenesulfonyl)-5-O-desosaminyl-erythromycilamine derivatives of the formula II, wherein R$^2$ is a C$_1$-C$_5$ alkyl radical, halogen or NH$_2$, which comprises reacting a compound of the formula I, wherein R is a C$_1$-C$_5$ alkyl radical, halogen or NHCOR$^1$ (R$^1$ being C$_1$-C$_5$ alkyl or phenyl), with diluted mineral acids in a convenient solvent (e.g. dimethylformamide, methanol) at room temperature.

The products may be isolated from the reaction mixture by such methods as extraction or crystallisation.

Since it is known that compounds of the class of erythromycines without the sugar cladinose have no antibacterial activity, but the compounds according to the invention have such an activity, being the hydrolysis products of parent substances in an acidic medium, so their activity and the activity of the parent substances in vitro may have a special meaning for their effect in vivo.

The invention is illustrated by the following Examples:

EXAMPLE 1

N-(4-chloro-benzenesulfonyl)-5-O-desosaminyl-erythromycilamine

N-(4-chloro-benzenesulfonyl)-erythromycilamine (3 g., 0.0033 moles) was dissolved in 1% methanolic HCl (300 ml.) and left at room temperature for 24 hours. The solution was subsequently evaporated in vacuo.

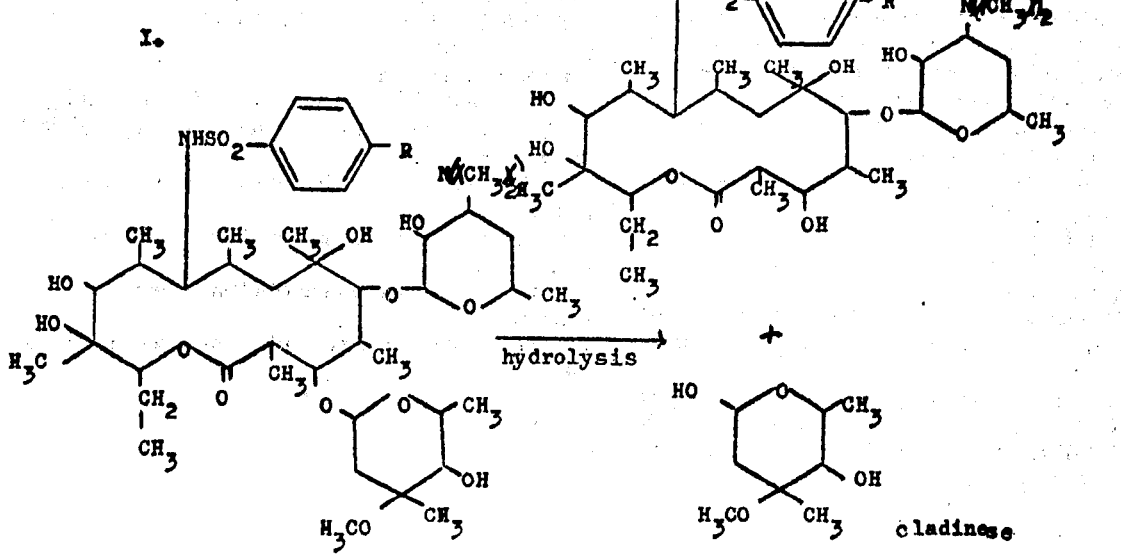

Preliminary bacteriological tests with the novel compounds obtained according to the invention showed that they have an activity on some pathogene microorganisms as well as a synergistic activity with trimethoprime (Table I).

TABLE I

| Compound | MIC in mcg/ml of the tested compounds | | |
|---|---|---|---|
| | E.coli 7920 | E.coli 8141 | Strept.haem. |
| DEASBr | 250 | 500 | 62.2 |
| DEASBr + T | 62.2 | 62.2 | 0.9 |
| DEASCl | 250 | 250 | 125 |
| DEASCl + T | 62.2 | 31.1 | 7.8 |
| DEASNH$_2$ | 125 | 125 | 62.2 |
| DEASNH$_2$ + T | 62.2 | 31.1 | 3.9 |
| DEAST | 125 | 125 | 62.2 |
| DEAST + T | 62.2 | 31.1 | 3.9 |

DEASBr = N-(4-bromo-benzenesulfonyl)-5-O-desosaminyl EA
DEASCl = N-(4-chloro-benzenesulphonyl)-5-O-desosaminyl EA
DEASNH$_2$ = N-(4-amino-benzenesulfonyl)5-O-desosaminyl EA
DEAST = N-(4-methyl-benzenesulfonyl)-5-O-desosaminyl EA
EA = erythromycilamine
T = trimethoprime The residue was dissolved in chloroform (8 ml.) and gradually added drop by drop under vigorous stirring to a mixture of saturated NaCl solution (12 ml.), 20% Na$_2$CO$_3$ solution (20 ml.) and saturated NaHCO$_3$ solution (12 ml.). After the separation of the layers, the aqueous layer was extracted with chloroform (3 × 10 ml.). The combined chloroform extracts were washed successively with a saturated NaHCO$_3$ solution (10 ml.) and saturated NaCl solution (10 ml.) and dried over K$_2$CO$_3$. After the elimination of chloroform, the residue was three times crystallized from chloroform petroleum ether, m.p. 148°–152°C.

Analysis for C$_{35}$H$_{59}$ClN$_2$O$_{11}$S. calc.: C 55.94%; H 7.91%; N 3.72%; S 4.26%. obt.: C 55.74%; H 8.14%; N 3.90%; S 4.10%. (M$^+$) = 750. $[\alpha]_D^{20}$ = −22.55° (1% solution in CHCl$_3$)

EXAMPLE 2

N-(4-methyl-benzenesulfonyl)-5-O-desosaminyl-erythromycilamine

N-(4-methyl-benzenesulfonyl)-erythromycilamine (3 g., 0.0034 moles) in 1% methanolic HCl (300 ml.) was left for 24 hours at room temperature. The solution was then evaporated in vacuo and the residue dissolved in chloroform (8 ml.). The chloroform solution was added drop by drop under vigorous stirring to a mixture of saturated NaCl solution (12 ml.), 20% $Na_2CO_3$ solution (20 ml.) and saturated $NaHCO_3$ solution (12 ml.). After vigorous stirring the layers were separated and the aqueous layer extracted with chloroform (3 × 10 ml.). the combined chloroform extracts were washed successively with a saturated $NaHCO_3$ solution (10 ml.) and saturated NaCl solution (10 ml.) and dried over $K_2CO_3$. After the elimination of chloroform, the residue was crystallised 3 times from chloroform/petroleum ether, m.p. 141°–145°C.

Analysis for $C_{36}H_{62}N_2O_{11}S$. calc.: C 59.15%; H 8.55%; N 3.83%; S 4.38%. obt.: C 59.21%; H 8.79%; N 4.00%; S 4.51%. $(M^+)$ = 730. $[\alpha]_D^{20}$ = −9.04° (1% solution in $CHCl_3$).

EXAMPLE 3

N-(4-bromo-benzenesulfonyl)-5-O-desosaminyl-erythromycilamine

N-(4-bromo-benzenesulfonyl)-erythromycilamine (3 g., 0.0031 moles) was dissolved in 1% methanolic HCl (300 ml.) and then left for 24 hours at room temperature. The solution was then evaporated in vacuo. The residue was dissolved in chloroform (8 ml.) and gradually added drop by drop under vigorous stirring to a mixture of saturated NaCl solution (12 ml.), 20% $Na_2CO_3$ solution (20 ml.) and saturated $NaHCO_3$ solution (12 ml.). After separating the layers, the aqueous layer was extracted with chloroform (3 × 10 ml.). The combined chloroform extracts were washed successively with a saturated $NaHCO_3$ solution (10 ml.) and a saturated NaCl solution (10 ml.) and dried over $K_2CO_3$. After the elimination of chloroform, the residue was crystallised 3 times from chloroform/petroleum ether, m.p. 151°–154°C.

Analysis for $C_{35}H_{59}BrN_2O_{11}S$. calc.: C 52.82%; H 7.47%; N 3.52%; S 4.03%. obt.: C 52.76%; H 7.71%; N 3.30%; S 4.07%. $(M^+)$ = 794 $[\alpha]_D^{20}$ = −23.78° (1% solution in $CHCl_3$)

EXAMPLE 4

N-(4-amino-benzenesulfonyl)-5-0-desosaminyl-erythromycilamine

N-(4-acetylamino-benzenesulfonyl)-erythromycilamine (3 g., 0.0032 moles) was dissolved in 1% methanolic HCl (300 ml.) and left for 24 hours at room temperature. The solution was then evaporated in vacuo. The residue was dissolved in chloroform (12 ml.) and added drop by drop under vigorous stirring to a mixture of saturated NaCl solution (12 ml.), 20% $Na_2CO_3$ solution (20 ml.) and saturated $NaHCO_3$ solution (12 ml.). After separating the layers, the aqueous layer was extracted with chloroform (3 × 10 ml.). The combined chloroform extracts were washed successively with a saturated $NaHCO_3$ solution (10 ml.) and a saturated NaCl solution (10 ml.) and dried over $K_2CO_3$. After the elimination of chloroform in vacuo, the residue was crystallised 3 times from chloroform/petroleum ether, m.p. 165°–169°C.

Analysis for $C_{35}H_{61}N_3O_{11}S$. calc.: C 57.43%; H 8.40%; N 5.74%; S 4.38%. obt.: C 56.52%; H 7.85%; N 5.00%; S 3.70%. $(M^+)$ = 731. $[\alpha]_D^{20}$ = −10.98° (1% solution in $CHCl_3$).

What we claimed is:
1. An N-(4-$R^2$-benzenesulfonyl)-5-0-desosaminyl-erythromycilamine, wherein $R^2$ is a $C_1$-$C_5$ alkyl radical, halogen or $NH_2$.
2. The erythromycilamine of claim 1, wherein $R^2$ is methyl.
3. The erythromycilamine of claim 1, wherein $R^2$ is bromine.
4. The erythromycilamine of claim 1, wherein $R^2$ is chlorine.
5. The erythromycilamine of claim 1, wherein $R^2$ is $NH_2$.

* * * * *